United States Patent
Petkar et al.

(10) Patent No.: US 10,006,059 B2
(45) Date of Patent: Jun. 26, 2018

(54) SELECTIVE MICROBIAL PRODUCTION OF XYLITOL FROM BIOMASS BASED SUGAR STREAM WITH ENRICHED PENTOSE COMPONENT

(71) Applicant: PRIVI BIOTECHNOLOGIES PRIVATE LIMITED, Mumbai, Maharashtra (IN)

(72) Inventors: Manish Petkar, Mumbai (IN); Shweta Pawar, Mumbai (IN); Arvind M. Lali, Mumbai (IN)

(73) Assignee: PRIVI BIOTECHNOLOGIES PRIVATE LIMITED, Navi Mumbai, Maharashtra (IN)

(*) Notice: Subject to any disclaimer, the term of this patent is extended or adjusted under 35 U.S.C. 154(b) by 164 days.

(21) Appl. No.: 14/424,669

(22) PCT Filed: Aug. 28, 2013

(86) PCT No.: PCT/IN2013/000523
§ 371 (c)(1),
(2) Date: Feb. 27, 2015

(87) PCT Pub. No.: WO2014/045297
PCT Pub. Date: Mar. 27, 2014

(65) Prior Publication Data
US 2015/0218598 A1    Aug. 6, 2015

(30) Foreign Application Priority Data
Aug. 28, 2012 (IN) .......................... 2495/MUM/2012

(51) Int. Cl.
| | |
|---|---|
| C12P 7/14 | (2006.01) |
| A23L 29/30 | (2016.01) |
| C12P 7/18 | (2006.01) |
| C12N 1/16 | (2006.01) |
| A61K 38/00 | (2006.01) |

(52) U.S. Cl.
CPC . *C12P 7/18* (2013.01); *C12N 1/16* (2013.01)

(58) Field of Classification Search
None
See application file for complete search history.

(56) References Cited

U.S. PATENT DOCUMENTS

| | | | |
|---|---|---|---|
| 2009/0004704 A1* | 1/2009 | Kim | C12P 7/18 435/105 |
| 2010/0297704 A1* | 11/2010 | Li | C12P 19/14 435/72 |
| 2011/0159560 A1* | 6/2011 | Donaldson | C12N 15/01 435/165 |
| 2012/0231514 A1* | 9/2012 | Geertman | C12P 7/18 435/158 |
| 2013/0183729 A1* | 7/2013 | Huang | C12P 7/18 435/158 |

OTHER PUBLICATIONS

Rao K. (2008) Fermentation Biotechnology, www.fbae.org/2009/FBAE/website/special topics_general_issues_fermentation_biotechnology.html, pp. 1-8.*
Affleck R.P. (2000) Recovery of Xylitol from Fermentation of Model Hemicellulose Hydrolysates Using Membrane Technology, Thesis of MS in Biological System Engineering, Virginia Polytechnic Institute and State University, pp. 1-114).*
SAMIGE (2008) De microbiologia General, pp. 1-98.*
West, Thomas P: "Xylitol production by *Candida* species grown on a grass hydrolysate", World Journal of Microbiology and Biotechnology, Kluwer Academic Publishers, DOI, vol. 25, No. 5, Jan. 4, 2009, pp. 913-916, XP019690956, ISSN:1573-0972.
Choi, et al: "Production of xylitol in cell recycle fermentations of *Candida tropicalis*", Biotechnology Letters, Springer, vol. 22, No. 20, Oct. 1, 2000 (Oct. 1, 2000), pp. 1625-1628, XP002418758, ISSN: 0141-5492, DOI:10.1023/A:1005693427389.
Kwon, et al: "Increase of Xylitol Productivity by Cell-Recycle Fermentation of Candida tropicalis Using Submerged Membrane Bioreactor", Journal of Bioscience and Bioengineering, vol. 101, No. 1, Jan. 1, 2006, pp. 13-18, XP028042334, ISSN: 1389-1723, DOI:10.1263/jbb.101.13.
Santos, et al:"Influence of aeration rate and carrier concentration on xylitol production from sugarcane bagasse hydrolyzate in immobilized-cell fluidized bed reactor", Process Biochemistry 40 (2005) 113-118, Elsevier, doi:10.1016/j.procbio.2003.11.045.

* cited by examiner

*Primary Examiner* — Manjunath N Rao
*Assistant Examiner* — Samuel W Liu
(74) *Attorney, Agent, or Firm* — Drinker Biddle & Reath LLP

(57) ABSTRACT

The present invention utilizes yeast *Candida tropicalis* (NRRL 12968) for xylitol production, as an alternative and unexplored strain with high bioconversion rate and stability at higher initial xylose concentration. Different parameters are optimized for batch fermentation of xylose to xylitol such as initial xylose concentration, aeration (vvm), agitation (rpm), percent inoculum addition, and oxygen transfer rate. Maximum xylitol yield of 0.7 g/g of xylose is obtained with 3.33% inoculum, 250 g/l of initial xylose concentration, 0.2 vvm of aeration rate, and two stage agitation strategy comprising of 500 rpm for 0-24 hrs and 400 rpm for 24-72 hrs at not more than 72 hrs of fermentation time. The present invention coins a novel process mode of fermentation where the batch process is extended with continuous fermentation at optimum dilution rate of 0.02/hr with effective residence time of 52 hrs. Productivity of 'batch followed by continuous' process is 2.5 gm/lit/hr which is 1.34 times higher than batch and/or continuous process alone.

22 Claims, No Drawings

SELECTIVE MICROBIAL PRODUCTION OF XYLITOL FROM BIOMASS BASED SUGAR STREAM WITH ENRICHED PENTOSE COMPONENT

FIELD OF INVENTION

The present invention relates to a method for production of xylitol from xylose (pentose sugar) obtained from variety of biomass such as grain bran, wood chips, corn cob & stalk, baggase and lignocellulosic biomass. A specific aspect of the invention relates to a method for production of xylitol by fermentation of lignocellulosic biomass hydrolysate and to the use of high initial xylose concentration for higher xylitol production in an effectively shorter conversion time.

BACKGROUND OF THE INVENTION

The pentahydric alcohol xylitol is a sugar alcohol, with significant application in food and confectionary industry as low calorie sweetener. It is widely distributed throughout nature in small amounts, with some of the best sources being fruits, vegetables, berries, mushrooms, lettuce, hardwoods, and corncobs. Human body produces 5-10 gms of xylitol from food source using established energy pathways. Although widely distributed in nature, its presence in low concentration makes it uneconomic to produce xylitol on commercial scale from such natural sources.

Xylitol has numerous advantages including the same sweetness as sucrose but with one-third fewer calories and no unpleasant aftertaste. After addition its negative heat of dissolution imparts a cool and refreshing sensation in the oral cavity, making it a popular sweetener for candies and sweets. Xylitol is cariostatic and even a non-carcinogenic substance. Xylitol finds favor with diabetic patients as it is metabolized independently from insulin in the human body (J. WEI, Q. YUAN, T WANG, Le WANG, *Front. Chem. Eng. China* 2010, 4(1):57-64). It has lower glycemic index value of 13 as against glucose with 100. Xylitol has also been shown to have therapeutic properties and reportedly builds immunity, fights against chronic degenerative diseases, is anti-aging, and has no known toxic levels.

The present invention relates to the microbial production of xylitol, from wood xylose as an enriched fraction of pentose sugar obtained from biomass, by an unexplored wild type *Candida* strain. More particularly, the invention relates to a novel process developed using a wild strain of *Candida tropicalis* for xylitol production with high yield and productivity. The invention relates to a process that uses wild type strain of *Candida tropicalis*, wherein the use of wild type strain always favors over genetically modified one from regulation point of view and overcomes issues related for the product being labeled under food category norms. The present invention also explores *Candida tropicalis* (NRRL 12968) to an extent which is capable of fermenting pentose sugar at higher rate and that can be achieved using different strains of same species currently known to the art.

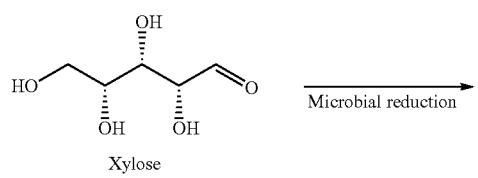

Xylose → Microbial reduction

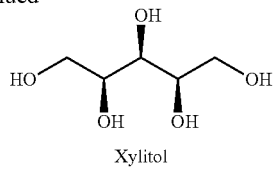

Xylitol

The importance of xylitol and its application in different industries require methods for maximum production of this sugar alcohol in an efficient manner. As xylitol is present in low concentrations in vegetables or fruits, its extraction is uneconomical from these sources. Thus xylitol can be produced via the direct reduction of xylose sugar in presence of suitable reducing agents using two main methods: direct reduction by synthetic chemical method and by natural microbial route.

Commercially xylitol is produced by chemical reduction of xylose, a hydrolysate fraction of hemicellulose present in woods, rice straw, millet, etc. An example of this process is described in the U.S. Pat. No. 4,008,285, in which the production of xylitol on a commercial scale is carried out by acid hydrolysis of pentosan-containing raw materials such as wood, corncobs, straw, bran, and cottonseed hulls. The hydrolysis of xylitol is usually carried out using Raney nickel catalyst ($NiZAl_2O_3$) at high temperature (80-140° C.) and pressure (up to 50 atm). One limitation of the chemical process is the difficulty of separation and purification of xylose or xylitol from hydrolysates containing other polymer sugars derived from hemicellulose fractions (Jeffries T. W., Kurtzman C. P., *Enzyme Microbial Technology*, November 1994, Vol. 16, Issue 11: 922-932). Multistep separation techniques, including mechanical filtration and chromatography are required to obtain pure xylitol. These processes adversely affect the cost of production for a yield in the range of 50-60%. Furthermore, such processes involve high temperature and high-pressure associated risks. Waste disposal due to use of acid or alkali is another major concern that is associated with chemical production of xylitol (E. Winkelhausen and S. Kuzmanova, *Journal of fermentation and bioengineering*, 1998, Vol. 86, no. 1, 1-14). These factors make the chemical methods for the routine production of xylitol difficult, expensive and inefficient.

Recently microbial production of xylitol is explored in literature which offers cost effective downstream processing that can reduce manufacturing cost (Rivas B. et al, *Enzyme Microb. Technol.*, 2003, 31:431-438). Such process would reduce the need for purified xylose, producing high pure, easy to separate product, and be adaptable to wide variety of raw material source from different geographical locations.

Most of the prior art methods reported in the literature shows application of yeast as biochemical catalyst for xylitol production because they are considered to be the best xylitol producers among microorganisms. Screening of more than 30 yeast strains revealed that yeast from genus *Candida*, such as *C. guilliermondii* VTT-C-71006, *C. tropicalis* ATCC 1369 and *C. tropicalis* ATCC 9968 are best xylitol producers (Ojamo, H, Ph.D. *Thesis Helsinki University of technology, Espoo, Finland*, 1994).

One of such methods described in prior art, using xylose fermenting yeast *Candida tropicalis* ATCC 13803 uses initial xylose concentration of 15% (PCT/IN2009/000027). The reported method discloses xylose fermentation in water solution with 50% of sugar conversion and 50% of yield in 196 hrs. Similar work has been reported utilizing *Candida tropicalis* ATCC 13803 wherein the initial Xylose concentration reported was 10% which is at lower side as compared to the earlier report (Patent No. KR100259470).

Another method reported in prior art used *Candida tropicalis* ATCC 9968 which has utilized higher initial xylose concentration of 5%-30% than previous reported processes (PCT/FI1990/000015).

Patent No. KR100199819 describes the use of *Candida tropicalis* KFCC 10960 with initial xylose concentration of 5-12%. One of prior art method reported 173 g/l of xylitol production from initial 200 g/l of xylose concentration in 120 hrs of fermentation using indigenously isolated yeast strain of genus *Candida* (T. Ikeuchi, M. Azuma, J. Kato, H Ooshima, *Biomass and Bioenergy*, 1999, 16, 333-339).

One of such methods described in prior art, using xylose fermenting yeast *Candida tropicalis* ATCC 750 (equivalent to NRRL 12968) yields less than 50% of xylitol from xylose mixture obtained from biomass hydrolysate (Thomas P. West, *World J. Microbiol. Biotechnol*, 2009, 25:913-916). The invention reports maximum product yield of 0.43 (gm of xylitol/gm of xylose) in 120 hrs of fermentation.

One of such methods described in prior art, using xylose fermenting yeast *Candida tropicalis* ATCC 7349 reports very low xylose concentration in the fermentation broth with lower xylitol yield. The initial xylose concentration used in the prior art process was 30 g/liter and yields less than 40% of xylitol from xylose mixture obtained from biomass hydrolysis (SAROTE S, MICHAEL S, MANFRED R, *Journal of Fermentation and Bioengeering*, 1995, Vol. 80, No. 6, 565-570).

Despite significant amount of prior art work, development of commercially feasible microbial production process has remained elusive for number of reasons. Those prior art methods reported in literature had either one or more of different drawbacks such as lower initial substrate concentration, poor conversion and molar/gram yield, and overall process productivity which do not reach the levels necessary for a commercial process. Thus the present invention describes a novel, cost efficient, and high yielding process, wherein higher xylose concentration can be used for commercial xylitol production at better economics.

SUMMARY OF THE INVENTION

The present invention relates to a method for production of xylitol from xylose obtained from variety of biomass, wherein xylitol yield of 0.7 g/g of xylose is obtained. The culture used for bioconversion is *Candida tropicalis* NRRL-12968, obtained from Northern Regional Research Center (hereafters refer as NRRL). Initial xylose concentration used for bioconversion reaction is in the range of 20-35% and glucose in the range of 0.5-1.5%. With such high initial xylose concentration, bioconversion time required for xylitol production is not more than 72 hrs with effective productivity of 1.91 gm of xylitol/hr/liter of fermentation broth. The present invention is upgraded to outcome a more inventive and novel technology for high throughput and better economics. The invented batch fermentation technology is further upgraded to 'continuous' and/or 'batch followed by continuous' mode, wherein the residence time of 46-64 hrs and dilution rate of 0.015-0.025/hr gives optimum productivity of 2.5 gm/lit/hr of xylitol.

One of the aspects of the present invention is to provide a process for microbial fermentation of xylose to xylitol using *Candida tropicalis*, wherein the process comprises: culturing the yeast strain and then transferring in production fermentor having xylose containing production medium. The process is carried out using batch mode followed by continuous' mode, wherein the residence time of 46-64 hrs and dilution rate of 0.015-0.025/hr gives optimum productivity of 2.5 gm/lit/hr of xylitol.

Another aspect of the present invention is to provide a process for a process for microbial production of xylitol from xylose containing biomass, wherein the process comprises: growing of yeast strain in a solid medium; inoculating the yeast strain obtained from above step in a seed medium containing seed fermentor; culturing the yeast stain by transferring in production fermentor having xylose containing production medium; wherein fermentation of said xylose containing biomass is carried out with yeast strain capable of converting xylose to xylitol; and removing the yeast strain from said production medium and recycling it for continuous production of xylitol.

DETAILED DESCRIPTION OF INVENTION

The present invention relates to a process for microbial production of xylitol from xylose containing biomass using strain of *Candida tropicalis*, wherein said process uses an unexplored strain from NRRL with high xylose tolerance level and higher xylitol production capacity. The xylose fermenting yeast strain used in this method is *Candida tropicalis*, obtained from NRRL culture bank with accession number 12968. The equivalent strains deposited in other strain bank with different accession number such as ATCC 750, 7349, reported in prior art had drawbacks of very low xylose intake up to 3% with very low xylitol production not exceeding 40%.

Thereafter the reported wild type strain in present invention is explored for initial Xylose intake and found to tolerate xylose concentration as high as 350 g/l or 35% of xylose concentration which is far more better than the reported strains in prior art.

The method reported in the present invention utilizes optimized concentration of xylose at 20-35% in production fermentor which is critical for the reported yeast growth. Increasing initial xylose concentration results in increase xylose uptake and hence xylitol formation (Sirisansaneeyakul S, Staniszewski M, Rizzi M, *J. Ferment. Bioeng*, 1995, 80, 565-570). High xylose concentration induces xylitol formation, favoring xylitol at the expense of ethanol production. At the same time for high productivity it is important that the amount of xylose converted to xylitol and the amount of xylitol available for further metabolism need to be well balanced (Eleonora W, Samual A, Slobodanka K, *Bulletin of the Chemists and Technologists of Macedonia*, Vol 22, No. 1, pp 47-54, 2003). This may provide a balance way of generating required cofactors through different steps of the metabolic pathway.

The strain used for present invention is obtained from the open culture collection of NRRL with accession no. 12968. The present invention reports a novel method for the production of xylitol by employing used strain NRRL12968, wherein the reported method is economical and commercially viable. The present invention reports a novel method, wherein the strain, an equivalent of ATCC 750 reported in prior art, can be used at high xylose concentration with selective production of xylitol where the overall tolerance of the strain has increased at commercially acceptable level. The initial xylose concentration used in the present study is in the range of 20-35%, preferably 25%. The reported invention describes a high yielding novel method producing 0.65-0.7 gm of xylitol/gm of xylose at airflow rate of 0.2 volume per volume of media per minute (hereafter refer as vvm) within 48-72 hrs of bioconversion time.

The method reported in the invention utilizes 0.2 vvm of constant air flow rate. Aeration plays an important role in the reported method for conversion of xylose to xylitol. High degree of aeration promotes cell growth on account of further oxidation pathway and enters into Krebs cycle for energy production than for xylitol. This is being detrimental to xylitol accumulation in fermentation broth (Walther T, Hensirisak P, Agblevor F. A., *Bioresource Technology*. 2001, 76(3): 213-220). Other way under limited oxygen conditions biomass formation was low, thereby decreasing xylitol production in broth.

The reported invention describes a novel approach and an efficient method for balancing the oxygen demand of yeast cells for biomass production verses the xylitol. It is reported that the oxygen transfer rate (OTR) from the gaseous phase to liquid phase and further from liquid phase to cell membrane is driven by the agitator velocity. Since the high agitation speed reports higher OTR as compared to the low agitation and shows exponential cell growth because of higher oxygen availability at cellular level. Thus a novel two stage agitation strategy is developed in the present invention to get maximum xylitol production at significant biomass formation.

The present invention describes a variable agitation condition at constant aeration rate, where in the first 24 hrs cell growth is promoted by keeping higher agitation rate of 500 rpm. The later stage is maintained at 400 rpm to induce xylitol accumulation over biomass. The novel approach reported in the present invention helps in balancing the oxygen demand to induce xylitol accumulation along with required cell growth. The novel two stage agitation strategy necessitates the need of 'batch followed by continuous' process, wherein the stage I used has significant role to bring cells in their highly productive stage, and the later stage II facilitates high productive continuous fermentation by maintaining cells in their active form.

The process described in the present invention is operated in batch mode for initial 65-75 hrs of fermentation and later operated in continuous mode with 1.34 time higher productivity than batch mode alone. The optimal residence time for batch mode is 65 hrs whereas that of continuous mode is 52 hrs. Optimum dilution rate at which continuous cell purging system operated is 0.02/hr.

One object of the present invention is to provide a process for microbial production of xylitol from xylose containing biomass using *Candida tropicalis* (NRRL 12968) to an extent which is capable of fermenting pentose sugar at higher rate and that can be achieved using different strains of same species.

Another object of the invention is to provide a process for biotransformation xylose to the xylitol with cost efficient, and high yielding process, wherein higher xylose concentration can be used for commercial xylitol production at better economics.

Yet another objective of present invention is to provide a process for microbial production of xylitol from xylose containing biomass using *Candida tropicalis* with higher initial substrate concentration, better conversion and molar/gram yield, and increase the overall process productivity to reach the levels necessary for a commercial process.

Another object of the invention is to provide a process for production of xylitol from xylose containing biomass with cost effective downstream processing that can reduce manufacturing cost.

Another object of the present invention is to provide a process to provide a process for microbial production of xylitol from xylitol containing biomass with mild reaction condition and environmentally benign.

One of the embodiments of the present invention provides a process for microbial fermentation of xylose containing biomass to xylitol, wherein said process comprises growing of yeast strain in a solid medium; inoculating the yeast strain obtained from above step in a seed medium containing seed fermentor; culturing the yeast strain from above step by transferring in production fermentor having xylose containing production medium; wherein fermentation of said xylose containing biomass is carried out with yeast strain capable of converting xylose to xylitol; and removing the yeast strain from said production medium and recycling it for continuous production of xylitol.

In another embodiment of the present invention there is provided microbial production of xylitol from xylose containing biomass using a yeast strain, wherein the said yeast strain may be *candida tropicalis*, having NRRL Accession No. 12968.

In yet another embodiment of the present invention there is provided a process for bioconversion of xylose to xylitol using a yeast strain, wherein concentration of xylose used may be in the range of 20-35% (w/v), preferably at 25% (w/v) and conversion of 250 g/l of xylose to 175 gm/l of xylitol may be not more than 72 hrs.

In another embodiment of invention there is provided a process for microbial fermentation of xylose containing biomass to xylitol, wherein composition of seed medium may be 1% glucose (w/v), 0.3% Yeast extract (w/v), 0.3% Malt extract (w/v), 0.5% peptone (w/v).

In one of the most preferred embodiment of the present invention, growth of seed culture is carried out in Erlenmeyer flask in the volume ratio of 5 and autoclaved for 20 minutes at standard conditions and after autoclaving, media is inoculated with optimized quantity of *Candida tropicalis* cell suspension.

In yet another embodiment of the present invention, the seed culture inoculum may be grown at 30° C. and 275 rpm for 18 hrs with optical density of the grown seed media at 18 hrs of incubation with 20× dilution may reach to 0.6-0.7 OD units at 640 nm.

In another embodiment of the present invention, the optimized protocol for preparing cell suspension may be formulated by maintaining *Candida tropicalis* cells on MYGP Agar at 4° C., suspending in sterile distilled water to make a dense suspension, adding the cell suspension into autoclaved seed media at pre-calculated dilution to achieve final OD of 0.1 to 0.2 OD units at 640 nm.

In another embodiment of the present invention, the solid medium used for cell growth may be MYGP agar plate, which is made up of 3 g/l yeast extract, 3 g/l malt extract, 5 g/l bacto-peptone, 10 g/l glucose and 22 g/l agar.

In one of the most preferred embodiment of the present invention there is provided a process for microbial production of xylitol from xylose containing biomass using *Candida tropicalis* culture, wherein said biomass may be hydrolysate of grain bran which is selected from the group consisting of rice and maize, corn cob, rice straw, wheat straw, cotton stack, oilseed waste, wood chips, lignocellulosic biomass.

In yet another embodiment of the present invention, the hydrolysate of grain bran may be used as main carbon source.

In another embodiment of the present invention, the carbon source used may be lignocellulosic biomass hydrolysate containing xylose along with glucose.

In another embodiment of the present invention, the fermentation may be carried out in a production medium, wherein xylose concentration is in the range of 20-35% (w/v), most preferably 25% (w/v).

In yet another embodiment of the present invention, the utilized seed culture may be grown for not more than 18 hrs of inoculation age where the culture is in logarithmic phase as concluded in growth curve studies, which is a mandatory requirement for high xylitol productivity.

In yet another embodiment of the present invention, the optimum cell density equivalent to 0.67 g/l (w/v) of cell concentration obtained in seed fermentor may be transferred to production fermentor at the optimized concentration of 3.33%.

In one of the embodiment of the present invention there is provided a process for microbial production of xylitol from xylose containing biomass, wherein composition of production medium may be 20-35% equivalent xylose (w/v), obtained from biomass hydrosylate, 5-15% glucose (w/v), 2.5-7.5% yeast extract (w/v), 5-15% peptone (w/v) and salts comprising 0.2-1% $KH_2PO_4$, 0.2-1% $MgSO_4.7H_2O$, 0.2-1% $(NH_4)_2SO_4$.

In yet another embodiment of the present invention, the fermentation may be carried out in batch mode or continuous mode or batch mode followed by continuous mode, most preferably batch mode followed by continuous mode.

In yet another embodiment of the present invention, the microbial fermentation may be carried out at temperature in the range of 28-32° C., most preferably at 30° C. and pH in the range of 5-7, most preferably 5.5 to 6.0.

In another embodiment of the present invention, the microbial fermentation may be performed at the aeration rate in the range of 0.1 to 0.5 vvm, most preferably 0.2 vvm.

In one of the most preferred embodiment of the present invention there is provided a process for microbial production of xylitol from xylose, wherein fermentation may be performed at an agitation speed of 500 rpm for initial 0-24 hrs of batch mode fermentation which favors cell growth; and 400 rpm for next 24-72 hrs of batch mode fermentation, most preferably 41-72 hrs, for accumulation of xylitol and furthermore kept constant in continuous mode till final harvest of the fermentation.

In another embodiment of the present invention, the fermentation may be carried out for about 60-72 hrs for batch mode, most preferably for 65 hrs and for continuous mode after 65 hrs about of batch mode.

In another embodiment of the present invention there is provided a process for microbial production of xylitol from xylose containing biomass using *Candida tropicalis*, wherein the process comprises removing the yeast strain from the production medium and recycling it for continuous fermentation resulting in continuous production of xylitol.

In another embodiment of the present invention there is provided a process for microbial production of xylitol from xylose containing biomass using yeast strain, wherein the optimum dilution rate for continuous mode of the process may be in the range of 0.015-0.025/lit, most preferable 0.02/lit.

In yet another embodiment of the present invention, the optimum residence time for continuous mode fermentation may be in the range of 46-65 hrs, most preferably 52 hrs.

In yet another embodiment of the present invention, the optimum productivity of the novel mix mode fermentation may be in between 1.8-2.5 gm/liter/hr, most preferably 1.87 gm/liter/hr for batch mode; and 2.5 gm/liter/hr for continuous mode of overall fermentation.

In one of the embodiment of the present invention, the cells growth rate may be maintained at constant logarithmic phase by continuously purging of cells at optimized dilution rate and residence time of xylose during continuous mode, while the substrate concentration is maintained constant throughout the process.

In another embodiment of the present invention, the cells may be continuously purged out along with broth maintaining their active log phase.

In another embodiment of the present invention, the consumption of xylose substrate and product formation may be monitored by High Performance (pressure) Liquid Chromatography equipped with Biorad Aminex HPX-87H Ion Exclusion Column. Thus dry cell density is estimated by calibration curve prepared by measuring optical density at 640 nm and dry cell weight.

In another embodiment of the present invention, the overall yield of product may be 65-70%, most preferably 65%.

Advantages:
1) The present invention provides a process involving batch mode followed by continuous mode fermentation which is more economical than either of batch and/or continuous process alone.
2) The novel approach reported in the present invention helps in balancing the oxygen demand to induce xylitol accumulation along with required cell growth.
3) The present invention provides a novel two stage agitation strategy to get maximum xylitol production at significant biomass formation.
4) The present invention provides a process for recovery and recycling of microorganism making the process cost effective and economically feasible.

EXAMPLES

The following examples illustrate the present invention and will enable others skilled in the art to understand it more completely. It should be understood, however, that the invention is not limited solely to the particular examples given below.

Example 1

*Candida tropicalis* NRRL 12968 was grown on MYGP agar plate containing 3 g/l Yeast extract, 3 g/l Malt extract, 5 g/l Bacto-peptone, 10 g/l Glucose and 22 g/l Agar. Yeast strain was then inoculated into seed medium containing 3 g/l Yeast extract, 3 g/l Malt extract, 5 g/l Bacto-peptone and 10 g/l Glucose of pH 6.0. 3.33% of 18 hr grown seed was inoculated to production media. Production media contains 20% (w/v) equivalent xylose obtained from maize bran hydrolysate, 1% glucose (w/v), 0.5% yeast extract (w/v), 1% peptone (w/v) and salts 0.05% $KH_2PO_4$, 0.05% $MgSO_4.7H_2O$, 0.05% $(NH_4)_2SO_4$. The medium was adjusted between 5.5-6.0 pH. Temperature of fermentor was maintained at 30° C. An aeration rate of 0.2 vvm was maintained in fermentor. The gradient agitation speed comprising of, 500 rpm for initial 24 hrs followed by 400 rpm for next 42 hrs was applied for fermentor. Fermentation was continued for 66 hrs and monitored for substrate consumption and products formation. At the end of 66 hr, fresh media with 20% xylose is continuously added at dilution rate of 0.02/hr with effective residence time of 52 hrs. At the same time cells along with product are continuously removed at flow rate equal to xylose addition flow rate. The analysis was done by HPLC equipped with BIORAD Aminex HPX-87H Ion exclusion column (300×7.8 mm) and using RID detector. Cell concentration was monitored by turbidometry method at 640 nm on spectrophotometer. Xylitol obtained was 175 g/l from 250 g/l of xylose at 98% of conversion.

Example 2

Protocol described in Example 1 is repeated using lignocellulosic biomass hydrolysate as source of xylose. The lignocellulosic biomass hydrolysate contains xylose as major pentose sugar along with glucose which is used as one of carbon source in the fermentation. Other media components like yeast extract, bacto-peptone and salts are added as additional nutrient source. Hydrolysate pH was adjusted in between 5.5-6. Fermentation was carried out at 30° C., at 0.2 vvm of constant air flow rate. The gradient agitation speed comprising of, 500 rpm for initial 24 hrs followed by 400 rpm for next 42 hrs was applied for fermentor. Fermentation was continued for 70 hrs and monitored for substrate consumption and products formation. At the end of 70 hrs, fresh media with 20% xylose is continuously added at dilution rate of 0.015/hr with effective residence time of 64 hrs. At the same time cells along with product are continuously removed at flow rate equal to xylose addition flow rate. The analysis was done by HPLC equipped with BIORAD Aminex HPX-87H Ion exclusion column (300×7.8 mm) and using RID detector. Cell concentration was monitored by turbidometry method at 640 nm on spectrophotometer. Xylitol obtained was 130 g/l from 194 g/l of xylose at 97% of conversion.

Example 3

Protocol described in Example 1 is repeated using rice bran hydrolysate as source of xylose. Rice bran hydrolysate contains xylose as major pentose sugar along with glucose which is used as one of carbon source in the fermentation. Other media components like yeast extract, bacto-peptone and salts are added as additional nutrient source. Hydrolysate pH was adjusted in between 5.5-6. Fermentation was carried out at 30° C., at 0.2 vvm of constant air flow rate. The gradient agitation speed comprising of 500 rpm for initial 24 hrs followed by 400 rpm for next 42 hrs was applied for fermentor. Fermentation was continued for 70 hrs and monitored for substrate consumption and products formation. At the end of 70 hr, fresh media with 20% xylose is continuously added at dilution rate of 0.025/hr with effective residence time of 47 hrs. At the same time cells along with product are continuously removed at flow rate equal to xylose addition flow rate. The analysis was done by HPLC equipped with BIORAD Aminex HPX-87H Ion exclusion column (300×7.8 mm) and using RID detector. Cell concentration was monitored by turbidometry method at 640 nm on spectrophotometer. Xylitol obtained was 130 g/l from 200 g/l of xylose at 97% of conversion.

Example 4

Protocol described in Example 1 is repeated using commercial xylose 20% and co-substrate glucose 1%. Other media components like yeast extract, bacto-peptone and salts are added as additional nutrient source. Hydrolysate pH was adjusted in between 5.5-6. Fermentation was carried out at 30° C., at 0.2 vvm of constant air flow rate. The gradient agitation speed of 500 rpm for initial 24 hrs followed by 400 rpm for next 42 hrs was applied for fermentor. Fermentation was continued for 68 hrs and monitored for substrate consumption and products formation. The analysis was done by HPLC equipped with BIORAD Aminex HPX-87H Ion exclusion column (300×7.8 mm) and using RID detector. Cell concentration was monitored by turbidometry method at 640 nm on spectrophotometer. Xylitol obtained was 142 g/l from 196 g/l of xylose at 99% of conversion.

Example 5

Protocol described in Example 1 is repeated at varying RPM conditions using corn cob hydrolysate and with all the reported media components. Corn cob hydrolysate contains xylose as major pentose sugar along with glucose which is used as one of carbon source in the fermentation. Hydrolysate pH was adjusted in between 5.5-6. Fermentation was carried out at 30° C., at 0.2 vvm of constant air flow rate. The gradient agitation speed comprising of 400 rpm for 0-30 hr, 300 rpm for 30-48 hr and 250 rpm for 48-72 hrs was applied to the fermentor. Fermentation was continued for 72 hrs and monitored for substrate consumption and products formation. The analysis was done by HPLC equipped with BIORAD Aminex HPX-87H Ion exclusion column (300×7.8 mm) and using RID detector. Cell concentration was monitored by turbidometry method at 640 nm on spectrophotometer. Xylitol obtained was 117 g/l from 200 g/l of xylose at 98% of conversion.

Example 6

Protocol described in Example 1 is repeated at fixed RPM conditions using maize bran hydrolysate and with all the reported media components. Hydrolysate pH was adjusted in between 5.5-6. Fermentation was carried out at 30° C., at 0.2 vvm of constant air flow rate. The fixed agitation speed of 200 rpm was applied to the fermentor. Fermentation was continued for 166 hrs and monitored for substrate consumption and products formation. The analysis was done by HPLC equipped with BIORAD Aminex HPX-87H Ion exclusion column (300×7.8 mm) and using RID detector. Cell concentration was monitored by turbidometry method at 640 nm on spectrophotometer. Xylitol obtained was 141 g/l from 220 g/l of xylose at 97% of conversion.

Example 7

Protocol described in Example 1 is repeated at 2% inoculum using maize bran hydrolysate as source of xylose. Maize bran hydrolysate contains xylose as major pentose sugar along with glucose which is used as one of carbon source in the fermentation. Other media components like yeast extract, bacto-peptone and salts are added as additional nutrient source. Hydrolysate pH was adjusted in between 5.5-6. Fermentation was carried out at 30° C., at 0.2 vvm of constant air flow rate. The gradient agitation speed of 500 rpm for initial 24 hrs followed by 400 rpm for next 24 hrs was applied for fermentor. Fermentation was continued for 48 hrs and monitored for substrate consumption and products formation. The analysis was done by HPLC equipped with BIORAD Aminex HPX-87H Ion exclusion column (300×7.8 mm) and using RID detector. Cell concentration was monitored by turbidometry method at 640 nm on spectrophotometer. Xylitol obtained was 61 g/l from 205 g/l of xylose at 52% of conversion.

Example 8

Protocol described in Example 1 is repeated at 10% inoculum using maize bran hydrolysate as source of xylose.

Maize bran hydrolysate contains xylose as major pentose sugar along with glucose which is used as one of carbon source in the fermentation. Other media components like yeast extract, bacto-peptone and salts are added as additional nutrient source. Hydrolysate pH was adjusted in between 5.5-6. Fermentation was carried out at 30° C., at 0.2 vvm of constant air flow rate. The gradient agitation speed of 500 rpm for initial 24 hrs followed by 400 rpm for next 42 hrs was applied for fermentor. Fermentation was continued for 66 hrs and monitored for substrate consumption and products formation. The analysis was done by HPLC equipped with BIORAD Aminex HPX-87H Ion exclusion column (300×7.8 mm) and using RID detector. Cell concentration was monitored by turbidometry method at 640 nm on spectrophotometer. Xylitol obtained was 97 g/l from 187 g/l of xylose at 72% of conversion.

Example 9

Protocol described in Example 1 is repeated with 30% equivalent xylose using maize bran as source of xylose. Maize bran hydrolysate contains xylose as major pentose sugar along with glucose which is used as one of carbon source in the fermentation. Other media components like yeast extract, bacto-peptone and salts are added as additional nutrient source. Hydrolysate pH was adjusted in between 5.5-6. Fermentation was carried out at 30° C., at 0.2 vvm of constant air flow rate. The gradient agitation speed of 500 rpm for initial 24 hrs followed by 400 rpm for next 142 hrs was applied for fermentor. Fermentation was continued for 166 hrs and monitored for substrate consumption and products formation. The analysis was done by HPLC equipped with BIORAD Aminex HPX-87H Ion exclusion column (300×7.8 mm) and using RID detector. Cell concentration was monitored by turbidometry method at 640 nm on spectrophotometer. Xylitol obtained was 191 g/l from 298 g/l of xylose at 97% of conversion.

We claim:

1. A process for microbial production of xylitol from biomass containing xylose comprising:
    a) growing in a solid medium a yeast strain capable of converting xylose to xylitol;
    b) inoculating the yeast strain obtained from step (a) in a seed fermentor containing seed medium wherein said yeast stain is a species of *Candida*; and
    c) fermenting the yeast strain from step (b) by transferring said yeast strain from step (b) to a production fermentor, the production fermentor having a production medium comprising a xylose-containing biomass, said fermenting said xylose-containing biomass being carried out in two sequential stages: in a first stage of batch mode of fermentation, fermenting said xylose-containing biomass with the yeast strain from step (b) at an agitation speed of about 500 rpm for at least 1 hr to no more than 24; and in a second stage, performing a batch followed by continuous mode of fermentation comprising: fermenting said xylose-containing biomass with the yeast strain from first stage in batch mode for an additional 24 to 72 at about 400 rpm; and then continuously adding xylose-containing biomass to the production fermentor while continuously removing xylitol product from the production fermentor in continuous mode at about 400 rpm at a rate of xylose-containing biomass addition being equivalent to a rate of xylitol removal, wherein the batch mode followed by continuous mode fermentation produces 1.8 g/L/hr to 2.5 g/L/hr of xylitol.

2. The process as claimed in claim 1, wherein the xylose-containing biomass is selected from the group consisting of: grain bran, rice, maize, corn cob, rice straw, wheat straw, cotton stack, oilseed waste, wood chips, baggase, lignocellulosic biomass, or hydrolysates thereof.

3. The process according to claim 1, wherein the xylose-containing biomass is lignocellulosic biomass enriched in at least one of the following: a pentose sugar polymer, a pentose hyrdosylate, an enriched fraction of hemicellulose from paper industry waste, or a commercial xylose.

4. The process as claimed in claim 1, wherein the production medium has a xylose concentration in the range of 20-35% (w/v).

5. The process as claimed in claim 4, wherein said production medium has a xylose concentration of 25% (w/v).

6. The process as claimed in claim 1, wherein said yeast strain is *Candida tropicalis*.

7. The process as claimed in claim 1, wherein said yeast strain is *Candida tropicalis* having NRRL Accession No. 12968.

8. The process as claimed in claim 1, wherein said inoculating of said yeast strain in step (b) is performed at 30° C., and 275 rpm for 18 hrs.

9. The process as claimed in claim 1, wherein said fermentation in the production fermentor is carried out at a temperature in the range of 28-32° C.

10. The process as claimed in claim 9, wherein said fermentation in the production fermentor is carried out at a temperature of 30° C.

11. The process as claimed in claim 1, wherein said fermentation in the production fermentor is carried out at a pH in the range of 5.0 to 7.0.

12. The process as claimed in claim 11, wherein said fermentation in the production fermentor is carried out at a pH in the range of 5.5 to 6.0.

13. The process as claimed in claim 1, wherein said fermentation is performed at an aeration rate in the range of 0.1 to 0.5 volume per volume of media per minute (vvm).

14. The process as claimed in claim 13, wherein said fermentation in the production fermentor is performed at the aeration rate of 0.2 vvm.

15. The process as claimed in claim 1, wherein the said fermentation in the production fermentor is carried out for about 60-72 hrs for batch mode fermentation.

16. The process as claimed in claim 15, wherein the said fermentation to the production fermentor is carried out for 65 hrs.

17. The process as claimed in claim 1, wherein the said fermentation in the production fermentor is operated in continuous mode after 65 hrs about of batch mode fermentation.

18. The process as claimed in claim 1, wherein the continuous mode of the process has a dilution rate in the range of 0.015-0.025/hr.

19. The process as claimed in claim 18, wherein the dilution rate is 0.02/hr.

20. The process as claimed in claim 1, wherein the continuous mode fermentation has a residence time in the range of 46-65 hrs.

21. The process as claimed in claim 20, wherein the residence time is 52 hrs.

22. The process as claimed in claim 1, wherein the batch mode fermentation produces 1.87 g/L/hr of xylitol; and the continuous mode fermentation produces 2.5 g/L/hr of xylitol.

* * * * *